(12) United States Patent
Dunlop

(10) Patent No.: US 7,883,480 B2
(45) Date of Patent: Feb. 8, 2011

(54) MOTION MONITORING APPARATUS

(76) Inventor: Colin Dunlop, 132A Cressy Road, East Ryde (AU) NSW 2113

( * ) Notice: Subject to any disclaimer, the term of this patent is extended or adjusted under 35 U.S.C. 154(b) by 0 days.

(21) Appl. No.: 11/938,938

(22) Filed: Nov. 13, 2007

(65) Prior Publication Data

US 2008/0091122 A1 Apr. 17, 2008

Related U.S. Application Data

(62) Division of application No. 10/009,663, filed as application No. PCT/AU00/00456 on May 15, 2000, now Pat. No. 7,294,112.

(30) Foreign Application Priority Data

May 13, 1999 (AU) .................................. PQ4916

(51) Int. Cl.
*A61B 5/08* (2006.01)
*A61B 5/103* (2006.01)
*A61B 5/117* (2006.01)

(52) U.S. Cl. ........................ 600/595; 600/534
(58) Field of Classification Search ................. 600/534, 600/535, 536, 587, 595, 301
See application file for complete search history.

(56) References Cited

U.S. PATENT DOCUMENTS

| | | | |
|---|---|---|---|
| 3,911,899 A | 10/1975 | Hattes | |
| 4,502,490 A | 3/1985 | Evans et al. | |
| 4,836,219 A | 6/1989 | Hobson et al. | |
| 4,969,459 A | 11/1990 | Gusako | |
| 5,195,531 A | 3/1993 | Bennet | |
| 5,280,791 A | 1/1994 | Lavie | |
| 5,410,297 A | 4/1995 | Joseph et al. | |
| 5,448,996 A | 9/1995 | Bellin et al. | |
| 5,751,214 A | 5/1998 | Cowley et al. | |
| 5,780,798 A | 7/1998 | Hall-Jackson | |
| 5,846,206 A | 12/1998 | Bader | |
| 5,862,803 A | 1/1999 | Besson et al. | |
| 6,233,472 B1 | 5/2001 | Bennett et al. | |
| 6,498,652 B1 | 12/2002 | Varshneya et al. | |
| 6,807,965 B1 | 10/2004 | Hickle | |

FOREIGN PATENT DOCUMENTS

| | | |
|---|---|---|
| EP | 0 691 105 A1 | 1/1996 |
| EP | 702978 A2 | 3/1996 |
| GB | 2227322 A | 7/1990 |
| GB | 2254691 A | 10/1992 |
| WO | WO 91/15997 | 10/1991 |

OTHER PUBLICATIONS

Lawrence et al. "The Development of a Tool to Access Neonatal Pain". Neonatal Network. Sep. 1993:12(6) 59-66.*

* cited by examiner

*Primary Examiner*—Max Hindenburg
*Assistant Examiner*—Jonathan M Foreman
(74) *Attorney, Agent, or Firm*—Davis & Bujold P.L.L.C.

(57) ABSTRACT

A motion monitoring apparatus and method for monitoring a patient under medical care. A sensor arrangement is provided in the form of a pad which the patient lies on. The sensor arrangement provides a signal which can be monitored to observe motion of the patient and provide an alarm should the motion meet certain predetermined conditions. The invention is particularly applicable for monitoring patients under sedation, recovering from anaesthesia, or in intensive care. The device is particularly useful for veterinary patients.

11 Claims, 5 Drawing Sheets

MOTION MONITORING APPARATUS

This application is a divisional application of U.S. patent application Ser. No. 10/009,663 file Feb. 8, 2002 now U.S. Pat. No. 7,294,112 which is a national stage completion of PCT/A000/00456 filed May 15, 2000, which claims priority from Australian Application Serial No. PQ 4916 filed May 13, 1999.

FIELD OF INVENTION

The present invention relates to an apparatus and method of monitoring animals or human patients under medical care.

Particularly, but not exclusively, the invention relates to an apparatus and method of monitoring patients who may be unconscious or semiconscious, undergoing medical procedures or having undergone medical procedures, and recovering from medical procedures, such as anaesthesia and sedation, or during intensive care or critical care.

The apparatus and method is particularly applicable to animal patient care, and the following description of the invention will be given with reference to an animal as a patient. The apparatus and method can be adapted for human patient care, however.

BACKGROUND OF INVENTION

In veterinary practice, animals require heavy sedation or general anaesthesia for any number of procedures where sedation or anaesthesia would not necessarily be required for a human patient. Note that in the following description and claims when "anaesthesia" is referred to it will be understood that "sedation" will also be covered, and vice versa. Generally, animals require sedation or anaesthesia to facilitate manipulative procedures (e.g. radiographs), for minor surgical procedures (e.g. dental procedures) and for major surgery (e.g. ovariohysterectomy, fracture repair, etc.). In fact, anaesthesia is required for about one third of "income generation" procedures. In busy practices this results in many animals recovering from anaesthesia each day, frequently with several animals recovering from anaesthesia at the same time. Because of economic and manpower needs, animals recovering from anaesthesia are not usually under continuous observation by a trained person. Frequently these animals recover in large recovery or treatment rooms where other procedures are occurring. Therefore, the veterinary staff "keep an eye" on the animals recovering from anaesthesia while their attention is otherwise diverted.

The objective of monitoring a patient recovering from anaesthesia is to detect changes such as:

shivering increasing chest excursions (rate or volume)

random body limb and neck movements chewing, especially if the patient is intubated.

All the above changes reflect increased muscle tone associated with increasing activity and awareness of the nervous system as patients recover from the "relaxed" state of general anaesthesia. Problems can occur if it is not realized that a patient is becoming aroused after anaesthesia or during critical care.

For example, animals recovering from anaesthesia frequently remain intubated (a tube passing through the mouth into the larynx and trachea, used to maintain an open airway) until their laryngeal function returns, such as when they swallow or cough. If intubated patients become conscious with the tube in place they usually become startled and start to chew the tube and to struggle. If they are not attended to and the tube removed, it can be "bitten off" with part of the tube remaining in the trachea.

Further, veterinarians need to know if the patient develops an airway obstruction. Whether intubated or not, semi-conscious animals (recovering from anaesthesia or during critical care) are at risk of developing airway obstructions which can result in hypoxia and death. This occurs because either an intubated patient may close its mouth/jaws on the endo-tracheal tube or a non intubated patient moves about and can collapse with it's head twisted in a position where the airway becomes obstructed.

In addition to monitoring state of consciousness in animals recovering from anaesthesia, veterinarians need to know that the patients temperature is returning to normal. Small animals, such as cats and dogs, have a relatively high surface area to body weight ratio and anaesthesia reduces muscle movement and shivering. Consequently hypothermia is the most common and potentially critical complication occurring during anaesthesia in small animals and during critical care of small semi-conscious patients. It is difficult to increase body temperature in patients that are already covered by sterile drapes for surgery particularly where a surgical procedure results in exposure of internal organs and cavities. Therefore once patients are placed in the recovery area their temperature is usually taken intermittently using a mercury or electronic thermometer and then efforts are made to increase their body temperature such as use of heating blankets, hot water bottles and heating lamps. While the goal is to prevent further decrease in body temperature and to warm the patient, it is also possible to induce hyperthermia and occasionally severe skin burns if patients treated with heating devices are not adequately monitored. Accidents often happen where there are a lot of patients to observe. This may, for example, result in severe burns to a patient being warmed excessively or further, hypothermia can develop in the case of patients who have lost too much body heat and rewarming temperature monitoring has not been adequate. With the current methods, intermittent monitoring using mercury or electronic thermometers, this is more likely to happen.

All the above problems are compounded where there are a lot of patients being monitored simultaneously in a recovery or treatment room. It is very difficult to "keep an eye" on all the patients at the same time, and it may be the case that an animal becomes aroused without the veterinary staff being aware. These problems may occur, therefore, and often do in practising veterinary hospitals.

SUMMARY OF INVENTION

From a first aspect, the present invention provides a method of monitoring a patient under medical care comprising the steps of providing a sensor arrangement which is arranged to detect motion of the patient, monitoring the motion of the patient by way of the sensor arrangement, determining whether the motion is indicative of patient arousal and providing an alarm should the motion be indicative of patient arousal.

Patient arousal may be indicated by bodily motion of the patient. As the patient becomes aroused they may start to "twitch" their limbs, for example. The present arrangement preferably detects that bodily motion and, therefore, indicates that the patient is becoming aroused. By "bodily motion", note that we mean any motion of the patient's body exclusive of motion of the chest wall due to respiration.

Preferably, the method of the present invention is applied for monitoring a patient during anaesthesia and recovery from anaesthesia or during intensive care.

Preferably, in the method of the present invention, an alarm is also provided when respiratory motion (motion of the chest wall and perhaps thoracic and of the body motion respiration, as opposed to bodily motion) of the patient increases, indicating that the patient is becoming aroused.

The alarm may be a visual alarm, audible alarm, a display or any other means for indicating that the motion is indicative of patient arousal.

Preferably the sensor arrangement includes a pad on which the patient lies, the pad mounting a sensor for monitoring motion of the patient. The pad may be of a similar construction to the arrangements used in SIDS (Sudden Infant Death Syndrome) monitors. Where the patient is an animal, in accordance with an embodiment of the present invention, the pad may be adapted for an animal to lie on. The pad preferably includes a piezo-electric sensor for detecting movement of the patient.

Note that the objective of a SIDS monitor is to detect either chest orthoracic movement or ventilation by measuring expired CO2, and to determine when respiration of a patient has slowed below a predetermined level or when respiration has stopped (indicating apnea).

In the case of the present invention, the sensor arrangement is preferably used to monitor for increased motion of the patient, indicative of the fact that the patient is becoming aroused, i.e., their respiratory motion is increasing to a more rapid state or to monitor for bodily motion, i.e., the patient is moving about (also indicative of arousal).

Preferably, in this aspect of the present invention, the motion of the patient is monitored by the following method:

The sensor arrangement is arranged so that an output from the monitor occurs in accordance with movement. For example, when the patient breaths, and the chest moves, an output signal is produced. Further if the patient's body moves (bodily motion as opposed to motion of the chest due to respiration), again a signal will be produced. The number of signals produced (note that by "signals" this includes variations in an otherwise constant signal which may be produced by the sensor arrangement, i.e., one variation equals an output signal) therefore varies according to the motion of the patient. When the patient is under sedation and breathing slowly and regularly, signals will be occurring at a regular rate. Signals from bodily motion will be imposed upon the regular rate respiratory signals, and will appear as an increase in rate of the signals. Similarly, increase in respiration, such as occurs when a patient is becoming aroused, will cause an increase in rate of the signals. In accordance with the method of the present invention, if the signal rate increases beyond a predetermined threshold, it is considered that either bodily motion is occurring or respiration is increased to such a rate implying arousal of the patient.

Preferably, a control means is provided and the method also includes the steps of setting a baseline level for the signal rate of the sensor arrangement. The baseline level is preferably set by taking the signal rate when the patient is sedated or anaesthetized and using that signal rate as the baseline. The upper threshold is then set at a predetermined level above the baseline rate, for example 20% above the baseline rate.

Note that motion of the patient may be monitored over time and any trends followed to determine whether a patient is becoming aroused or not.

In an alternative embodiment, the sensor arrangement may further include a conventional respiratory motion sensor, of the type presently used. These include such arrangements as a band which is passed around the patients chest and which includes an expansion spring. As the patients chest wall moves, the spring expands, varying the resistance of an electrical circuit. An alternative conventional respiratory motion detector comprises a pair of electrodes placed on either side of the patient's chest. When the electrodes move apart and together, in accordance with the chest motion of the patient due to respiration, signals can be obtained indicative of the rate of respiration. Other detectors include respiratory thermometers and end-expired carbon dioxide analyzers and others.

Signals from the respiration monitor can be compared with signals from the sensor pad arrangement to isolate the signals which are due to bodily motion. Bodily motion and motion due to respiration can, therefore in this embodiment, be monitored separately.

In a preferred embodiment of the present invention, an alarm may also be provided when the sensor arrangement indicates that the patient's motion falls below a predetermined level, i.e., that there may be an apnea situation or unconsciousness/death due to hypoxia caused by an airway obstruction. The major objective of the present invention, however, is to monitor for states of arousal, so that the patient can be attended to. An alarm (which may be visual or audible or both) is preferably arranged to indicate to an observer that it is time to attend to the patient and remove any tubes from their trachea and perform any other treatment which may be necessary.

Preferably, the temperature of the patient is also constantly monitored. In the prior art, temperature monitoring is intermittent, as discussed above. In the present invention, temperature is preferably monitored constantly, by use of a temperature monitor (which may be by temperature thermistor; rectal oesophagel or inter-digital probe placement) and an alarm is provided should the temperature fall outside predetermined ranges, preferably indicative of potential hypothermic or hyperthermic states.

Preferably a monitoring device includes control means for monitoring the signals from the sensor arrangement and temperature sensor (where one is utilized) and providing outputs on a visual display and also audibly. Preferably, the control means is mounted in a housing which is mountable to a housing (e.g., cage or cage door) containing the animal patient. The monitoring device is, therefore, associated with a particular animal patient and the visual alarm immediately attracts the attention of the operative to the correct patient.

The present invention further provides a device for monitoring a patient under medical care, comprising a sensor arrangement which is arranged to detect motion of the patient and a control means which is arranged to process signals received from the sensor arrangement to determine whether the motion is indicative of patient arousal and to provide an alarm should the detected motion be indicative of patient arousal.

The device preferably further includes means for receiving signals from a temperature sensor and providing an alarm for output if the temperature falls outside a predetermined range, preferably indicative of potential hyperthermic or hypothermic states. Preferably, the device also provides an alarm when the motion drops below a predetermined level or ceases, indicative of a state of apnea, as discussed above.

The control means is also preferably arranged to carry out any or all of the method steps discussed above.

The present invention further provides a system including a plurality of devices as discussed above, the sensor arrangements mounted with respect to housings containing animals, to monitor a plurality of animals under medical care.

The monitoring of motion of patients who are under intensive care or under critical care may also provide information additional to the state of consciousness of the patients. For example, when a conscious or semiconscious animal patient under care is in pain, bodily motion may either be absent or rhythmic and "jerky" (or could follow other patterns indicative of pain). Bodily motion can, therefore, be used as an indicator of level of pain in a patient.

Bodily motion can also be used to determine a number of other conditions, e.g., to provide evidence of normal sleep/wake cycles, patients with history of syncope (e.g., heart disease, diabetes).

Such an analysis of motion of a patient may be particularly useful with animal patients and young human beings that cannot vocalize their condition.

From a further aspect, the present invention provides a method of monitoring a patient under medical care comprising the steps of providing a sensor arrangement which is arranged to detect motion of the patient, monitoring the motion of the patient by way of the sensor arrangement and analyzing the motion of the patient to determine the medical condition of the patient.

The motion of the patient may be analyzed to determine whether or not the medical condition is indicative of pain. For example, rhythmic and jerky motion may be considered to be indicative of pain as, with a conscious patient, no movement may be indicative of pain.

Preferably, a trend analysis of the motion of the patient may be made. That is over a long term (hours and days) the motion may be monitored to follow the trend of the patient, e.g., the "painfulness" of the patient reducing over time, implying that they are responding to treatment. A trend analysis may provide an average rate of motion read out per day which a physician may use to track the condition of the patient. Such an analysis would be particularly useful for critical care applications where patients are recovering from major surgery, e.g., spinal fracture in a dog. The analysis could measure acute (short term) motion changes as well as long term changes.

Preferably, the sensor arrangement includes a pad positioned under the patient, as for the first aspect of the invention discussed above.

Preferably, a control means is provided which provides an output indicative of the motion of the patient over a period of time. The output may be graphical or the control means may also carry out a trend analysis and determine the condition of the patient. If the output is graphical, this can be delivered to a physician to enable the physician to track the medical condition of the patient.

The present invention further provides a device for monitoring a patient under medical care comprising a sensor arrangement which is arranged to detect motion of the patient and a control means which is arranged to process signals received from the sensor arrangement to analyze the motion of the patient, whereby to enable a determination of the medical condition of the patient.

The control means may provide a graphical output of the motion of the patient over a period of time or may provide an output indicative of a condition of the patient determined by the control means.

The sensor arrangement preferably includes a pad monitor, as discussed above.

With any of the aspects of the invention discussed above, preferably the output from the sensor arrangement may be used, via a control means, to control operation of a peripheral device in response to a determined medical condition of the patient or in response to the patient becoming aroused from sedation or anaesthesia. For example, an output could be provided to control a heating device to turn on or off a heating pad, to control a ventilator (e.g., a dog with tick paralysis) or to control a syringe pump turning on or off a flow of analgesic medication or treatment or therapy.

The output from the sensor arrangement may be transmitted to a computer, for the computer to provide the alarm or track and analyze the trend in the motion of the patient. The computer may be situated remotely (e.g., in another part of a hospital or even at the physician's place of residence) and the signals from the arrangement be transmitted to the computer at the remote location.

Preferably, when bodily motion is monitored, track is kept of the motion of all parts of the body and not just isolated parts of the body.

BRIEF DESCRIPTION OF THE DRAWINGS

The invention will now be described, by way of example, with reference to the accompanying drawings in which:

FIG. 3b is a view of a front panel of a device of FIG. 3a;

DETAILED DESCRIPTION OF THE INVENTION

Figure 1:
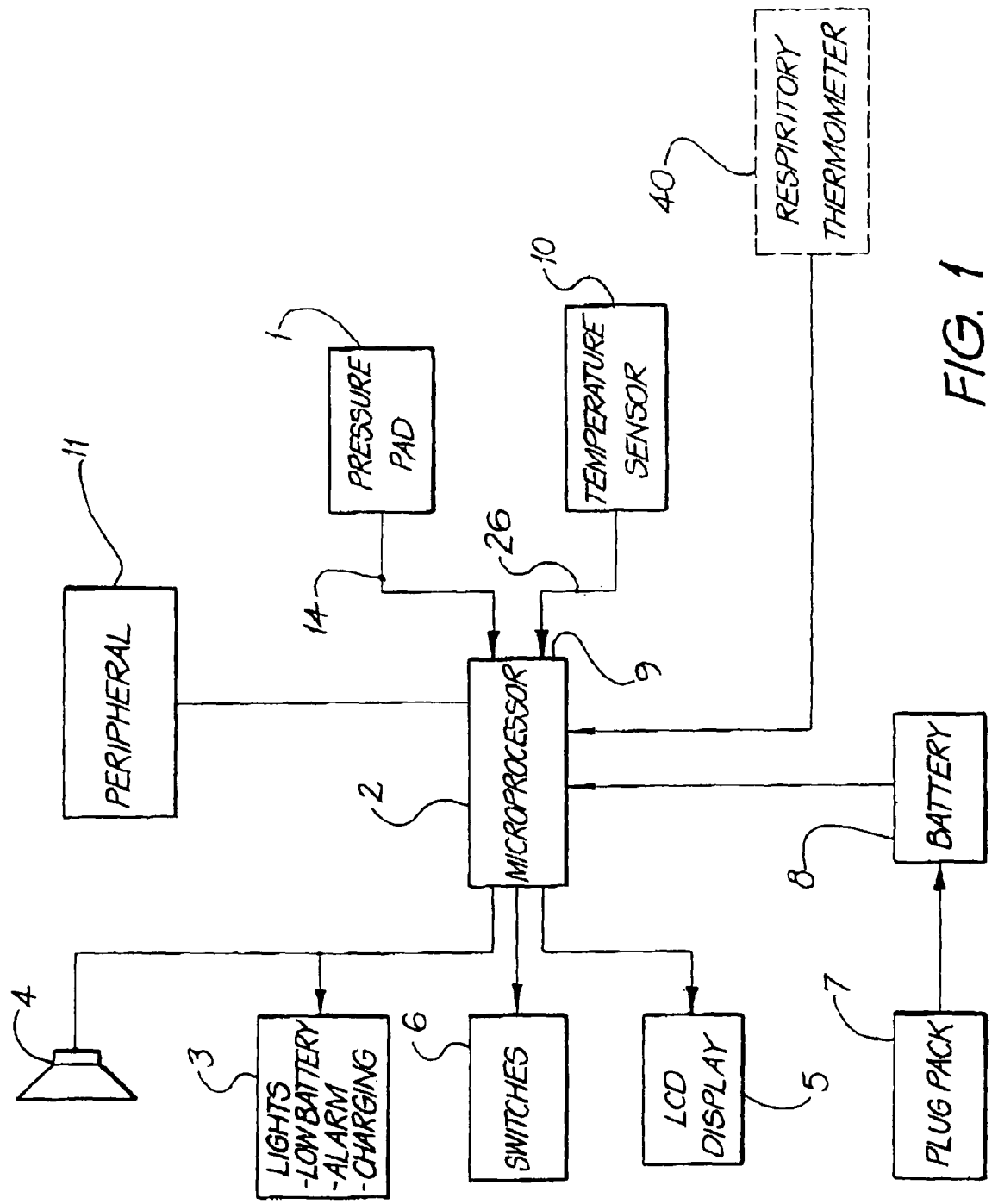
FIG. 1 is a block diagram of components of a device in accordance with an embodiment of the present invention.

Referring to the drawings, a device is illustrated which can be used to detect motion of a patient who is recovering from anaesthesia or sedation, or is in critical or intensive care and may be in an unconscious or semi-conscious state. The illustrated device is particularly designed for use with animals in veterinary hospitals, for example, but may be adapted for use with human beings.

The device comprises a sensor arrangement which is arranged to detect motion of the patient, in this particular embodiment being a pressure pad sensor arrangement 1, and a control means including a microprocessor 2 for monitoring the motion of the patient and determining whether the motion of the patient is indicative of the patient becoming aroused. Either bodily motion or increased respiratory motion of the patient may indicate that the patient is becoming aroused. Preferably, bodily motion and respiratory motion of the patient are monitored by the control means. In this embodiment, a visual alarm is provided by lights such as LEDs 3, and an audible alarm is provided by a loudspeaker 4.

The device also includes an LCD display 5 for providing visual display information; an input means such as switches 6 for setting input parameters and otherwise controlling the device; a power supply including a plug pack 7 enabling connection to the mains and also a battery 8, which is preferably a rechargeable battery. The device also includes an input 9 for receiving data from a temperature sensor 10, which may, for example, be a temperature thermistor (rectal, oesophagal or inter-digital probe placement), whereby the device can constantly monitor the temperature of the patient.

The device may be connected to a peripheral unit 11, for the purposes of controlling the peripheral unit via the microprocessor 2 in accordance with signals from the pressure pad monitor 1. For example, the peripheral unit 11 may be a ventilator, controllable by the microprocessor 2 to increase or decrease oxygen to a patient's lungs. Alternatively, it may be a syringe pump for adjusting a flow of analgesic. It may be any other type of device which it may be desirable to control in order to facilitate the condition of the patient.

Figure 2:
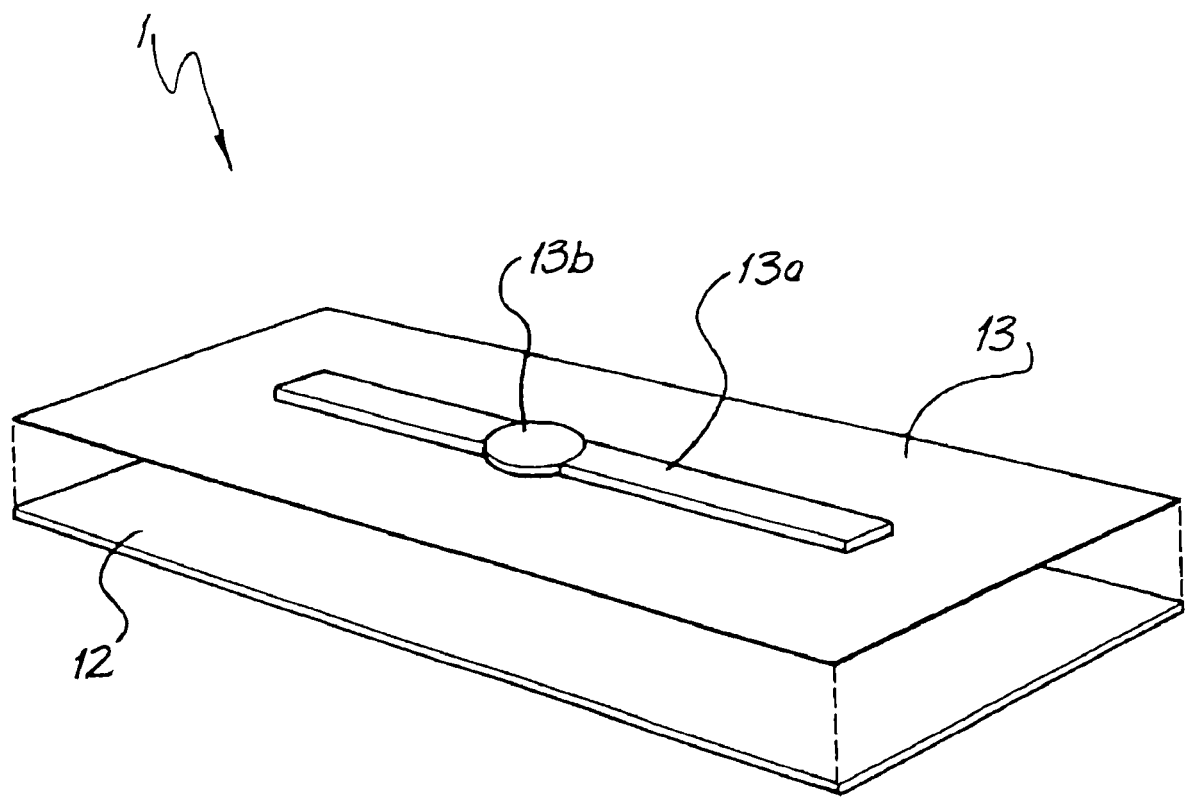
FIG. 2 is a schematic exploded diagram of a pressure pad motion sensor of the device of FIG. 1.

In more detail, referring to FIG. 2, an exploded view of a pressure pad, generally designated by reference numeral 1, is shown. Pressure pad 1 comprises a rigid base 12, which may be metal, for example. On top of the rigid base 12, a flexible membrane 13 is mounted (note that, in practice, the membrane will be directly on top of the rigid base 12). On the membrane, a further rigid strip 13a is laminated. The strip 13a is connected to a piezo-electric transducer 13b. When a change of pressure occurs on the strip 13a of piezo-electric transducer 13b, a signal will be produced. If a patient lies on the pad 1, therefore, any movement of the patient will produce a signal, whether the movement is due to respiratory movement (movement of the chest) or bodily motion. Note that the entire arrangement would be covered in flexible material, which may be plastics, for example (not shown). Piezo-electric transducer 13b is electrically connected to a cable 14 which is input to the microprocessor 2 (FIG. 1). The pressure pad 1 may be similar to the type of pressure pad used in earlier versions of SIDS (Sudden Infant Death Syndrome) monitors. The application of the pressure pad 1 in this embodiment of the invention, however, is different from what SIDS pad monitors were designed to do. SIDS pad monitors were arranged to watch for the absence of respiration (apnea). That is, when very low rate signals or no signals are being received, indicative of the fact that an infant may have stopped breathing or may have moved off the pad, then an alarm will be given. For the present invention, however, the use of the pressure pad 1 and associated control means is also to watch for bodily motion, or increased respiratory activity, both of which are indicative of the patient becoming aroused.

Figure 4A:
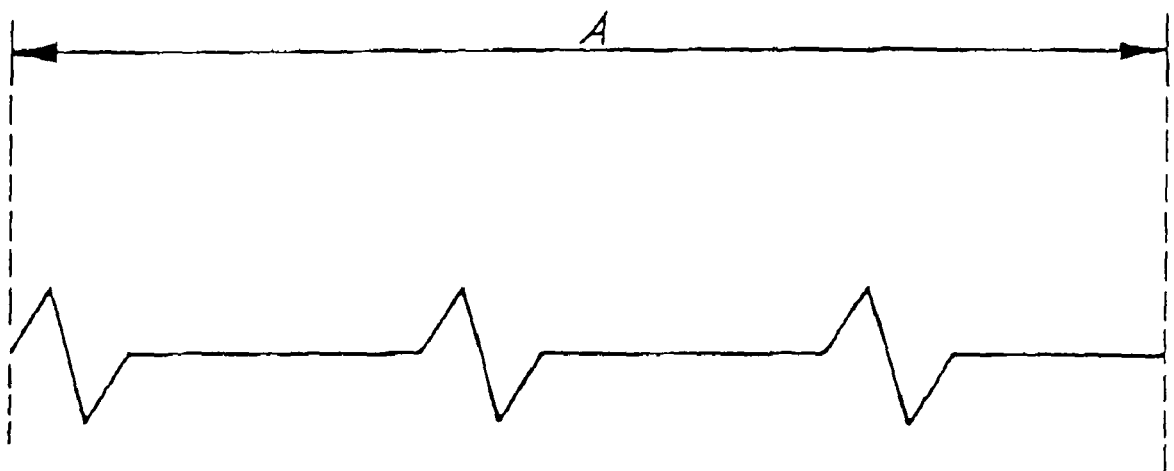
FIG. 4a and FIG. 4b are schematic examples illustrating signals which may be output by the motion sensor.
Figure 4B:
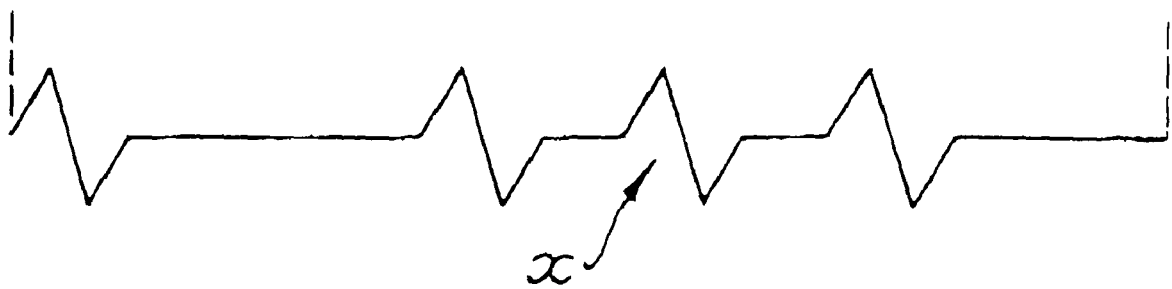

With the device of the present invention, the microprocessor 2 is programmed to watch for an increase in rate of signals produced by the transducer 13b. Referring to FIGS. 4a and 4b, FIG. 4a shows over a predetermined time period A the production of three signals by the transducer 13b. These signals are regularly spaced from each other and are indicative of, for example, a steady, slow respiration rate, indicating that the patient is unconscious.

In FIG. 4b, however, a further signal X has been produced within the time period A. Such a signal may be due to bodily motion of the patient on the pad 1, indicating that the patient is becoming aroused. The microprocessor 2 sees this extra signal or extra signals produced during the time period A as an increased rate. If this increased rate extends beyond a predetermined threshold, then an alarm will be given.

The increase in rate may be due to bodily motion or due to an increase in respiratory rate, both indicative of patient arousal.

For different patients, the thresholds at which alarms are given and the base respiration rate (base signal rate FIG. 4a) will vary. The device of the present invention is provided with a baseline set or "quick set" feature. When the baseline set function is actuated, the device samples the current motion (signals from the transducer 13b) which will usually be regular and slow when the patient is sedated or recovering from anaesthesia. This rate is determined to be the baseline rate. Thresholds of, for example, plus or minus 20% of the baseline rate is then automatically determined and, if the signal should increase above the upper threshold or fall below the lower threshold, then an alarm will be given.

In operation, when an alarm is given, an operative will attend the patient and see if the patient is becoming aroused. If the patient is not becoming aroused, the baseline function may again be actuated, adjusting the baseline rate to the new rate of motion of a patient (which may be a slightly higher rate of respiration, but still not sufficient to indicate arousal). The thresholds will then also be automatically adjusted.

Note that, alternatively to the baseline set feature, the device also includes means for manually setting a baseline and also threshold limits for the alarms. In a preferred embodiment, it also includes means for setting baselines depending upon type of patient, e.g., standard dog, standard cat, etc., and also threshold levels.

The monitor is also programmed to watch for apnea (lower threshold level). That is, if motion rate drops below a predetermined level (indicative of apnea), then the alarm will be given.

Further, the monitor is arranged to monitor the temperature of the patient by way of the temperature sensor 10 and give alarms should the body temperature fall above or below predetermined thresholds. Again, these thresholds are adjustable by way of the switches 6 so that the veterinarian can vary the parameters depending upon the patient. The thresholds are set to avoid hypothermia or hyperthermia in the patient. As well as manual setting of these parameters, there may also be provided preset parameters for different animal varieties, as with the motion monitoring function.

Figure 3A:
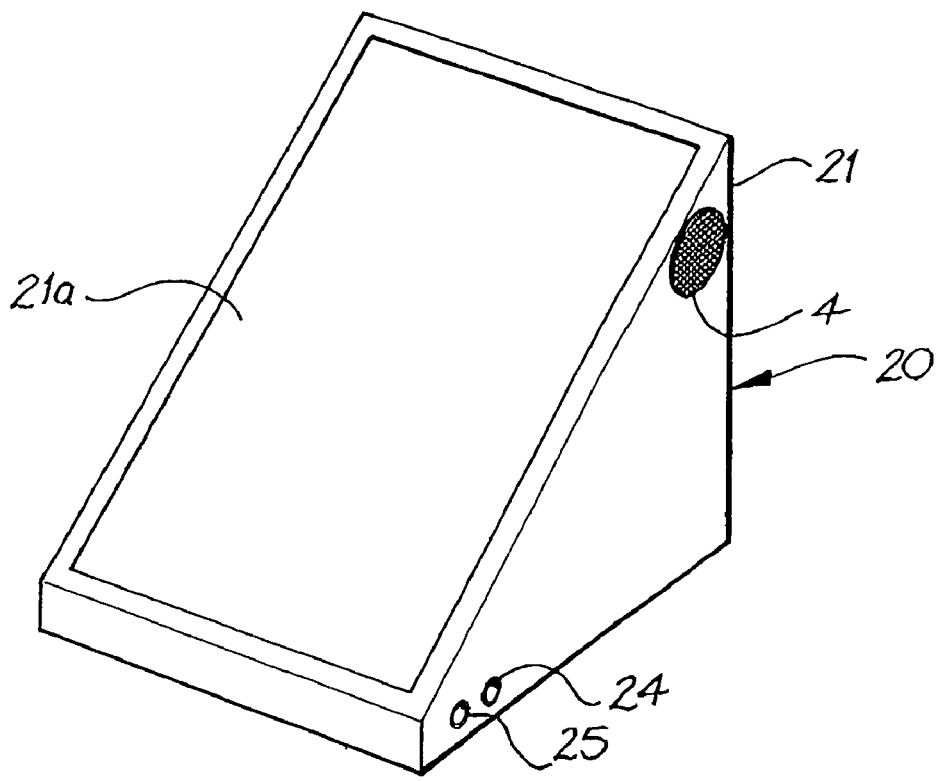
FIG. 3a is a perspective view of a device in accordance with an embodiment of the present invention.
Figure 3B:
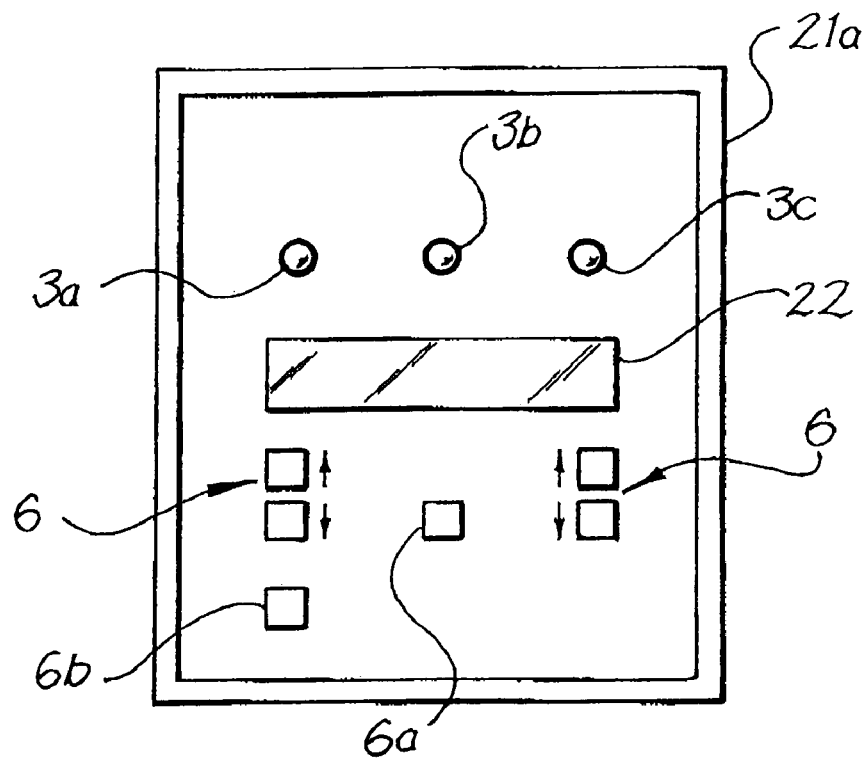

FIGS. 3a and 3b illustrate the device of FIG. 1 mounted in a housing 20. The housing 20 is a lightweight aluminium box or plastics and includes a hook (not shown) on a base 21 of the housing 20, for hooking the housing 20 on to the front of a cage containing an animal patient. Sockets 24 and 25 are provided for receiving respective cables 14 and 26 from the pressure pad 1 and the temperature sensor 10, respectively. The loud speaker 4 is also mounted to the housing 20 to enable emission of the audible alarm.

The front panel display 21a (see FIG. 3a) includes LEDs 3. The LED 3a indicates that the device is on charge. The LED 3b is a red LED providing visual alarm that the signal from the monitor is passed over the threshold level. The LED 3c indicates a low battery.

An LCD 22 is also provided which may provide a display of actual motion rate and temperature. Buttons 6 are also provided, including quick set button 6a (the same baseline rate), on/off switch B, etc.

As well as an operator being able to program the alarm settings by way of the switches 6, the microprocessor 2 is programmed with default high and low alarm settings for different animal patients as discussed above. If a rabbit is the patient, for example, a keyboard 23 will be actuated to produce the default settings for a rabbit (by actuating a button which may be a virtual button on a GUI on the LCD display 5). Similarly, for other animal patients.

Further, default high and low alarm settings for respiratory rate and temperature are programmed into the microprocessor to suit typical small animal patients recovering from anaesthesia. These settings are automatically enabled, without any action by the operator, on turning on of the monitor. The alarm functions are automatically returned to the default settings if the monitor is powered down, then restarted.

The default settings may, for example, be set at the following:
Respiration
High: 25 breaths per minute
Low: 5 breaths per minute.
Temperature
High: 40° C.

Low: 32° C.

If an alarm triggers, the monitor is arranged so that the auditory alarm can be turned off by actuating the keypad, but the visual alarm, light 3*b*, will stay on and the LCD screen 22 back light turns on until the alarm condition has been resolved. The visual alarm 3*b* enables an operator to rapidly determine from which cage or animal the alarm condition has occurred, even in a dimly lit recovery room.

Further, as discussed above, the monitor is arranged to have a "quick set" function, which when actuated automatically brackets the alarm settings to the actual parameters of a patient at any point in time. This allows the monitored alarms to be simply and instantly customized to any patient despite the wide variety of patient size and condition encountered in animal veterinary medicine. The quick set thresholds may be set as follows.

|  | LOW | HIGH |
|---|---|---|
| TEMPERATURE | −5% | +10% |
| MOTION | −20% | +20% |

As discussed above, heating devices are often used for animal patients with small body mass, to keep their temperature up as they are recovering from anaesthesia or undergoing critical care. In another embodiment (not shown), the monitor is connected to the power outlet for the heating device and is arranged to automatically shut off the heating device should the temperature rise to the threshold level. Further, it may be arranged to automatically switch on the heating device again when the temperature drops to a predetermined level (note that the predetermined level may not necessarily be the threshold level which indicates the onset of hyperthermia, but may be higher).

As well as an alarm, the peripheral device 11, such as a ventilator, for example, may be actuated when the predetermined threshold levels are reached, or when other predetermined threshold levels are reached.

The device may include a radio transmitter (not shown in this embodiment) for sending radio frequency signals to control the power outlet for the heating device or to control the peripheral device, as opposed to being hard-wired.

An alternative embodiment of the device enables analysis of the motion of the patient to determine their medical condition. As discussed in the preamble of this document, an analysis of the motion of a patient who is sedated or in critical care can tell a lot about the condition of the patient. An animal in pain, for example, will either remain totally still or will move in a rhythmic, "jerky" fashion. This is as opposed to an animal who is not in pain who would probably move in an irregular fashion over a relatively long period of time (e.g., a day). The painful animal is likely to remain immobilized or to move rhythmically for relatively long periods of time. The painless animal would just go about its normal processes, e.g., eating, walking around, lying down, etc. An analysis of motion of a patient over a period of time can, therefore, provide information about its medical condition. Trend analysis can be carried out of the motion to determine whether the patient's condition is, for example, improving or deteriorating.

In one embodiment of the present invention, the device of FIG. 1 provides an output of the rate of motion either to a display, a printer, or to a personal computer. A physician can study the display or the print out, to use this determine the medical condition of the patient. Alternatively, the PC can be programmed with a program analyzing the motion and providing an output which indicates what the condition of the patient is at any time, e.g., painful, normal, improving, deteriorating.

Output from the microprocessor 2, depending upon the detected motion may also control the peripheral device 11, such as a syringe pump for turning on and off analgesic flow in, e.g., painful animals.

Note that the pressure pad 1 could be made the same size as the bottom of an animal cage, for example, to ensure that total motion of the animal is tracked.

Figure 5A:
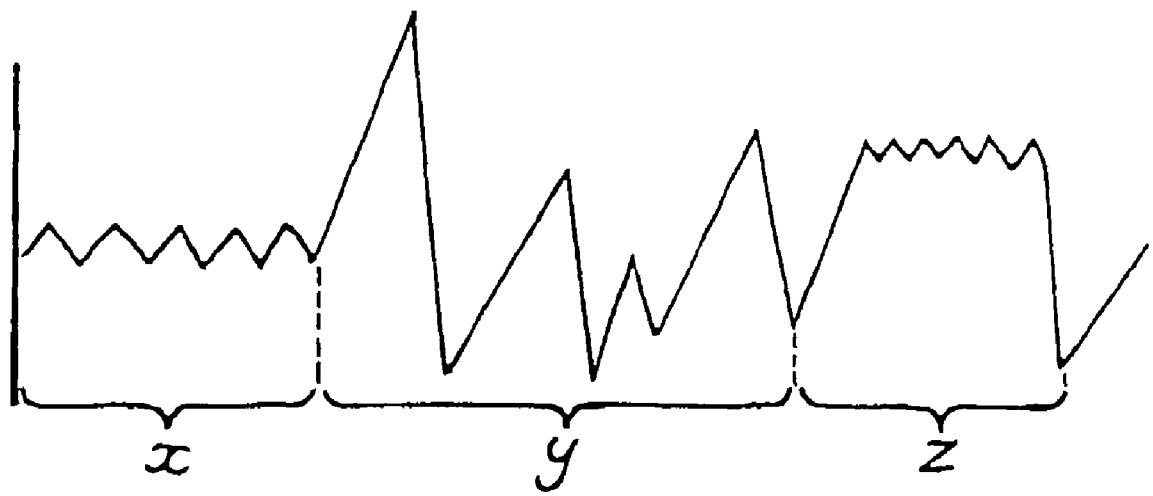
FIG. 5a and FIG. 5b are further schematic diagrams illustrating signals which may be output by an embodiment of the present invention for the purposes of determining a medical condition of a patient.

FIG. 5*a* is a schematic example of a print out over a period of time (say several hours) of motion for an animal which may be healthy. Period X is indicative of a healthy animal asleep; period Y of a healthy animal awake and moving around the cage; period Z of a healthy animal awake and sitting.

Figure 5B:
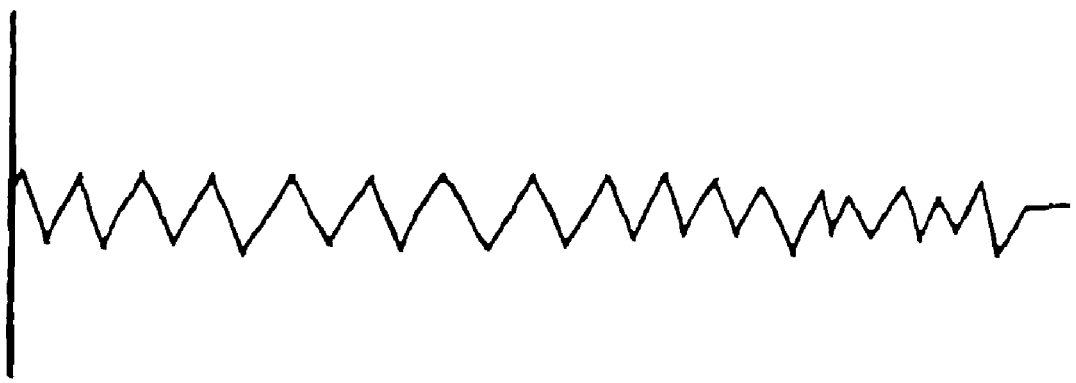

On the other hand, FIG. 5*b* illustrates the sort of regular motion (e.g., shivering) that may be observed with an animal in pain. This animal does not exhibit normal sleep/wake and activity cycles such as eating. Alternatively, an animal in sever pain may have no body movement at all (conscious, but still). So only the regular respiration movement would be observed.

Note that the waveforms 5*a* and 5*b* are for illustration only and it may be that the waveforms do not appear like this. The intention here is merely to demonstrate that the motion of a patient tracked over time can provide an indication of their medical condition which can be analyzed and used to determine medical treatment.

In the above described embodiments of the invention, a single monitor device, mounted in a housing is used for each animal patient. An alternative embodiment (not shown) receives signals from a plurality of patients to a single monitoring device which includes separate alarms for each patient, but which may include a single display. Such a monitoring device could easily be followed by a single person at a central monitoring station.

The device may be adapted for use with human patients.

The device may also be used during surgery.

In a further embodiment, the device may operate independently as a temperature monitor or a motion monitor. Preferably, the microprocessor 2 is aware of whether a temperature sensor or a pressure pad is present. If only one is present, the device will automatically then operate only as a temperature or pressure monitor, which ever device is present.

In the above embodiments, the sensor arrangement for monitoring motion is a pressure pad. It would be possible to use other sensor arrangements to monitor motion. For example, infra-red sensors could be placed in the space where the patient is housed (e.g., cage). A further alternative is a video camera.

In a further alternative embodiment, a conventional respiratory motion sensor may be used in conjunction with the pad sensor arrangement described above. Instead of using the pad sensor to monitor all motion (respiratory and bodily) the conventional respiration monitor is used to provide a signal indicative of respiratory motion, and this signal is processed and compared with the signal from the pad motion sensor, e.g., by subtraction. The remaining signal from the pad motion sensor is then, therefore, indicative of bodily motion only of the patient. Referring to FIG. 1, a respiratory thermometer 40 is shown schematically in ghost outline. Respiratory and bodily motion can be tracked separately.

The device may output signals to a computer. The computer may be situated so that a physician may monitor the device signals from their home, for example.

Further, the device itself may include an LCD monitor for displaying a trend waveform when monitoring for the medical condition of the patient.

Note that the monitor could be provided with a sensitivity control to control the sensitivity of the pad monitor, to cope with different sizes of patients, e.g., animal patients.

The alarm provided by the device may be audible or visual. The alarm may include any means which provides an indication that the patient is being aroused, and may include a visual monitor.

In the above embodiment, the sensor arrangement is a pad monitor. Other types of sensor arrangements may be used instead of a pad monitor, such as infra-red beams, for example.

Variations and modifications may be made to the invention as shown in the specific embodiments without departing from the spirit or scope of the invention as broadly described. The present embodiments are, therefore, to be considered in all respects as illustrated and not restrictive.

The invention claimed is:

1. A method of monitoring a patient under medical care, the method comprising the steps of:
providing a sensor arrangement which is arranged to detect motion of a head, limbs and trunk of the patient, and produce a motion signal in response to the motion of a patient, and
analysing the motion signal to determine whether or not the patient is displaying signs of painfulness,
wherein if the analysis of the motion signal determines that the motion includes rhythmic, repetitive motion of the head, the limbs or the trunk, a determination is made that the patient is displaying signs of painfulness.

2. The method in accordance with claim 1, wherein the step of detecting motion of the patient includes detecting respiratory motion of the patient and producing a motion signal in response to the respiratory motion.

3. The method in accordance with claim 2, further comprising the step of monitoring the respiratory motion and the bodily motion of the head, the limbs or the trunk of the patient by the same sensor arrangement.

4. The method in accordance with claim 2, further comprising the step of monitoring the respiratory motion and the bodily motion of the head, the limbs or the trunk of the patient by separate sensor arrangements.

5. The method in accordance with claim 2, further comprising the step of generating a single motion signal, as the motion signal, from a combination of the bodily motion of the head, the limbs or the trunk of the patient and the respiratory motion.

6. The method in accordance with claim 2, further comprising the step of generating the motion signal to include a first motion signal, generated from the bodily motion of the head, the limbs or the trunk of the patient, and a second motion signal, generated from the respiratory motion.

7. The method in accordance with claim 1, further comprising the step of using a non-human animal patient as the patient.

8. The method in accordance with claim 1, further comprising the step of using a human patient as the patient.

9. The method in accordance with claim 1, comprising the further step of controlling operation of a peripheral device in response to the analysis.

10. A device for monitoring a patient under medical care, the device comprising a sensor arrangement which is arranged to detect motion of the head, limbs and trunk of the patient and produce a motion signal in response to the motion, and a control means which is arranged to process the motion signal and analyse the motion signal, to determine whether or not the patient is displaying signs of painfulness, the control means is arranged to determine that the patient is displaying signs of painfulness if the motion signal is determined to include rhythmic repetitive motion.

11. A device for monitoring a patient under medical care, the device comprising a sensor arrangement which is arranged to detect motion of the head, limbs and trunk of the patient and produce a motion signal in response to the motion, and a control means which is arranged to process the motion signal and analyse the motion signal, to determine whether or not the patient is displaying signs of painfulness, the device is arranged to output a graphical output which indicates the rate of motion over a time period of the patient, which can be used to determine the painfulness of the patient.

* * * * *